United States Patent [19]

Mastromatteo et al.

[11] Patent Number: 6,028,331
[45] Date of Patent: Feb. 22, 2000

[54] INTEGRATED SEMICONDUCTOR DEVICES COMPRISING A CHEMORESISTIVE GAS MICROSENSOR

[75] Inventors: Ubaldo Mastromatteo, Cornaredo; Vigna Benedetto, Potenza, both of Italy

[73] Assignee: STMicroelectronics S.r.l., Agrate Brianza, Italy

[21] Appl. No.: 09/015,600

[22] Filed: Jan. 30, 1998

[30] Foreign Application Priority Data

Jan. 31, 1997 [EP] European Pat. Off. .............. 97830034

[51] Int. Cl.[7] .......................... H01L 23/58; H01L 27/14; H01L 29/82; H01L 29/84
[52] U.S. Cl. ............................. 257/253; 257/414; 338/34
[58] Field of Search .................................. 357/253, 414; 338/34

[56] References Cited

U.S. PATENT DOCUMENTS

| | | | |
|---|---|---|---|
| 4,535,316 | 8/1985 | Wertheimer et al. | 338/34 |
| 4,836,012 | 6/1989 | Doty et al. | 73/23 |
| 5,068,205 | 11/1991 | Baxter et al. | |
| 5,345,213 | 9/1994 | Semancik et al. | 338/34 |
| 5,576,563 | 11/1996 | Chung | 257/253 |
| 5,652,443 | 7/1997 | Kasai | 257/252 |
| 5,786,608 | 7/1998 | Lescouzeres et al. | 257/253 |

FOREIGN PATENT DOCUMENTS

WO 96/36869  11/1996  WIPO.

OTHER PUBLICATIONS

Moser, David and Henry Baltes, A High Sensitivity CMOS Gas Flow Sensor Based on an N–Poly/P–Poly Thermopile, DCS–vol. 40, Micromechanical Systems ASME Dec. 1992.

Shajii, Javad, Kay–Yip Ng, and Martin A. Schmidt, A Microfabricated Floating–Element Shear Stress Sensor Using Wafer–Bonding Technology, Journal of Microelectromechanical Systems, vol. 1, No. 2, Jun.1992.

Mutschall, D., C. Scheibe, and E. Obermeir, Basic Micro Module for Chemical Sensors with on Chip Heater and Buried Sensor Structure, The 8th International Conference on Solid–State Sensors and Actuators, and Eurosensors. IX Stockholm, Sweden, Jun. 25–29, 1995.

Haisma, J., G.A.C.M. Spierings, UK.P. Biermann and J.A. Pals, Silicon–On–Insulator Wafer Bonding–Wafer Thinning Technological Evaluations, Japanese Journal of Applied Physics, vol. 28 No. 8, Aug. 1989, pp. 1426–1443.

Stoffel, Axel M., Micromachining and ASIC Technology, Microelectronics Journal, 25 (1994) 145–156.

*Primary Examiner*—Mahshid Saadat
*Assistant Examiner*—Allan R. Wilson
*Attorney, Agent, or Firm*—Theodore E. Galanthay; David V. Carlson; Seed and Berry LLP

[57] ABSTRACT

To manufacture integrated semiconductor devices comprising chemoresistive gas microsensors, a semiconductor material body is first formed, on the semiconductor material body are successively formed, reciprocally superimposed, a sacrificial region of metallic material, formed at the same time and on the same level as metallic connection regions for the sensor, a heater element, electrically and physically separated from the sacrificial region and a gas sensitive element, electrically and physically separated from the heater element; openings are formed laterally with respect to the heater element and to the gas sensitive element, which extend as far as the sacrificial region and through which the sacrificial region is removed at the end of the manufacturing process.

25 Claims, 4 Drawing Sheets

INTEGRATED SEMICONDUCTOR DEVICES COMPRISING A CHEMORESISTIVE GAS MICROSENSOR

TECHNICAL FIELD

The invention relates to a process for manufacturing integrated semiconductor devices comprising a chemoresistive gas microsensor.

BACKGROUND OF THE INVENTION

As is known, chemical sensors detect the presence of gas on the basis of a chemical reaction which takes place between the molecules of the gas and a sensitive film. The chemical reaction depends significantly on the operating temperature which influences the effects of adsorption, desorption and diffusion of the gas in the film. Consequently, temperature is an important factor in optimizing the performance of the sensor, particularly as regards sensitivity, selectivity and response time. To guarantee optimum operation, therefore, the sensors are provided with means for regulating and controlling temperature.

Recently, integrated chemoresistive gas microsensors, the manufacture of which makes use of microelectronics techniques, have been proposed and produced. These microsensors have the following advantages: reduced manufacturing costs, low energy consumption in operation, high response times and integrability with the temperature control and output signal processing circuit.

Integrated gas microsensors using chemoresistive membranes based on tin oxide are appearing on the market; on the surface of such membranes, deposited on a wafer of semiconductor material machined using the technique of "bulk micromachining," described below, a chemical reaction takes place between the oxygen of the membrane and the gas to be detected which has the effect of changing the resistance of the film and thus enables the presence of the gas to be detected.

In order to operate correctly, such sensors must be maintained at temperatures of approx. 400° C., so they are provided with heater elements and must be thermally insulated from the rest of the chip, which includes the integrated signal processing and control circuit.

Various techniques for isolating the sensitive part from the rest of the chip are known in literature. The technique used historically consists of "bulk micromachining," comprising producing the sensitive part on top of or inside a dielectric layer deposited on a solid silicon wafer and removing a portion of solid silicon from the back of the wafer with wet etching methods. The dielectric layer performs the dual task of mechanically supporting the sensor and thermally insulating the sensor from the wafer of solid silicon. In the context of this technique prototypes have been produced with partial removal of the silicon from the area of the sensor, in which the excavation is carried out only on part of the thickness of the wafer, and prototypes which provide the total removal of the silicon at the area of the sensor (the etching reaches as far as the dielectric layer carrying the sensor element). As regards this second solution, reference may be made for example to the article entitled "Basic Micro-Module for chemical sensors with on chip heater and buried sensor structure" by D. Mutschall, C. Scheibe, E. Obermeier.

On the other hand the technique of bulk micromachining requires the presence of front-back machining processes and comprises particular demands for handling the chips which are such that it proves to be incompatible with current integrated circuit manufacturing methods.

Another proposed technique consists of "front micromachining" on the basis of which the wafer of solid silicon is etched from the front and a dielectric layer mechanically supports and thermally insulates the sensor element. In this respect, for the production of a different type of sensor, reference may be made for example to the article by D. Moser and H. Baltes entitled "A high sensitivity CMOS gas flow sensor based on an N-poly/P-poly thermopile," DSC-Vol. 40, Micromechanical Systems, ASME, 1992; furthermore, for a survey of the techniques of bulk and front micromachining, reference may also be made to the article entitled "Micromachining and ASIC technology" by Axel M. Stoffel in Microelectronics Journal, 25 (1994), pages 145–156.

This technique for producing suspended structures does, however, require the use of etching phases that are not very compatible with the current manufacturing processes used in microelectronics and does not therefore permit sensors and the related control and processing circuitry to be obtained on a single chip.

Furthermore, the use of dedicated SOI (Silicon On Insulator) substrates has been proposed, in which the starting wafer comprises a stack of silicon/silicon oxide/silicon, with the oxide selectively removed at the sensor area, forming an air gap. The excavations made from the front of the wafer at the end of the process phases to contact the air gap enable the sensor to be thermally insulated. In this respect, for a shear stress sensor, reference may be made for example to the article by J. Shajii, Kay-Yip Ng and M. A. Schmidt entitled "A Microfabricated Floating-Element Shear Stress Sensor Using Wafer-Bonding Technology," Journal of microelectromechanical systems, Vol. 1, No. 2, June 1992, pages 89–94. The method used for bonding (apart from the formation of the air gap) is further described in the article "Silicon-on-Insulator Wafer Bonding-Wafer Thinning Technological Evaluations" by J. Hausman, G. A. Spierings, U. K. P. Bierman and J. A. Pals, Japanese Journal of Applied Physics, Vol. 28, No. 8, August 1989, pages 1426–1443. Finally, the use of a dedicated SOI substrate is also described in European patent application No. 96830436.0 filed on Jul. 31, 1996 in the name of this applicant.

SUMMARY OF THE INVENTION

The object of the invention is to provide a manufacturing process and a chemoresistive gas sensor which do not have the disadvantages of the current techniques.

According to the invention, there are provided a process for manufacturing an integrated semiconductor device and a device itself, comprising a chemoresistive gas microsensor and an integrated device comprising a chemoresistive gas microsensor.

BRIEF DESCRIPTION OF THE DRAWINGS

For an understanding of the invention a preferred embodiment will now be described, purely by way of non-exhaustive example, with reference to the accompanying drawings, in which.

DETAILED DESCRIPTION OF THE INVENTION

Figure 1:
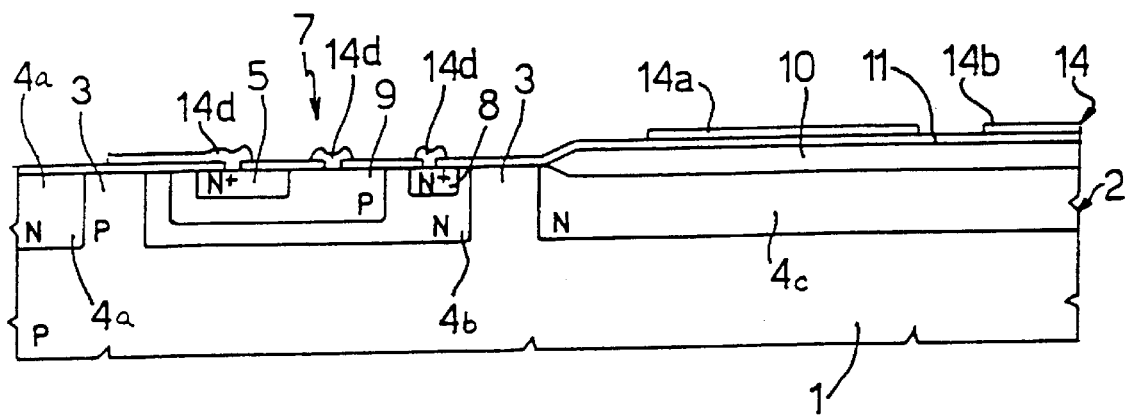
FIG. 1 shows the cross-section of a wafer of semiconductor material in an initial phase of the manufacturing process.

Initially a P-type single crystal silicon substrate is subjected to standard process phases for forming electronic components, whether bipolar or MOS, of integrated circuits. With reference to the numbering of FIG. 1, in particular, an N-type epitaxial layer 2 is grown on substrate 1. On the surface of the substrate 1, during the steps used to define and isolate in the active areas, a field oxide layer 10 is caused to grow over the portion that will have the heater 21 and sensor 25; in the epitaxial layer 2, P-type junction isolation regions 3 are formed to define N-type pockets 4a, 4b, 4c, . . . , inside which the active components of the device are formed.

In greater detail, the first pocket 4c (above which the sensor will subsequently be formed) is completely covered by the field oxide layer 10 whereas the pocket 4b houses an NPN-type transistor 7 forming part of the temperature control and output signal processing circuit. The transistor 7 has a collector region formed by the pocket 4b and by the N+ region 8, a P-type base region 9 and an N+ type emitter region 5.

As FIG. 1 shows, subsequently, a protective dielectric layer 11 (such as silicon nitride or BPSG, that is boron phosphorus silicon glass) is deposited over the entire surface. The contacts are then opened and a first metallic layer 14 is deposited.

Figure 2:
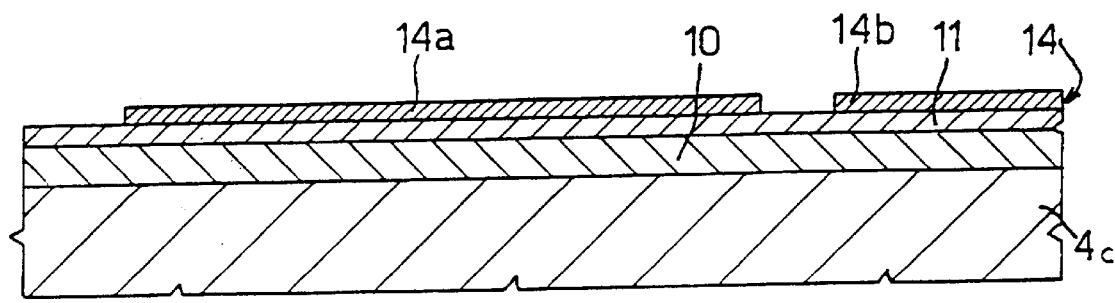
FIG. 2 shows a portion of the wafer of FIG. 1 on an enlarged scale.

The first metallic layer 14 is then defined so as to form at least one sacrificial region 14a of rectangular shape, situated on the area of the wafer intended for forming the sensitive element (i.e., above field oxide layer 10), two first contact regions 14b (only one of which is visible in FIG. 1) for forming the metallic connections of the heater, two second contact regions 14c (visible in FIG. 6) for forming the metallic connections of the sensitive element, as described below, and further regions 14d constituting the contact electrodes of the regions 5, 8, 9 of the transistor 7. The disposition of the regions 14a and 14b is easier to see in the enlarged scale view of FIG. 2.

Figure 3:
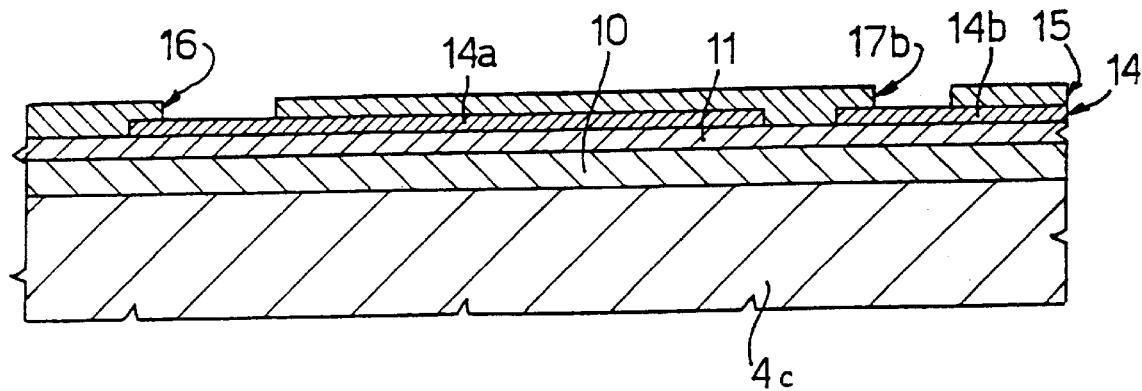
FIG. 3 shows the same section of FIG. 2 in a different step of the manufacturing process.

As FIG. 3 shows, an intermetallic dielectric layer 15 is deposited and defined so as to form etching openings 16 through which the sacrificial region 14a will successively be removed, openings 17a for the contacts of the sensitive element (visible in FIG. 6), openings 17b for the contacts of the heater as well as the openings (not shown) required for the control circuitry. As clear from the subsequent FIG. 4, the openings 16 are disposed in the vicinity of (and inside) the vertices of the rectangle formed by the sacrificial region 14a.

Figure 4:
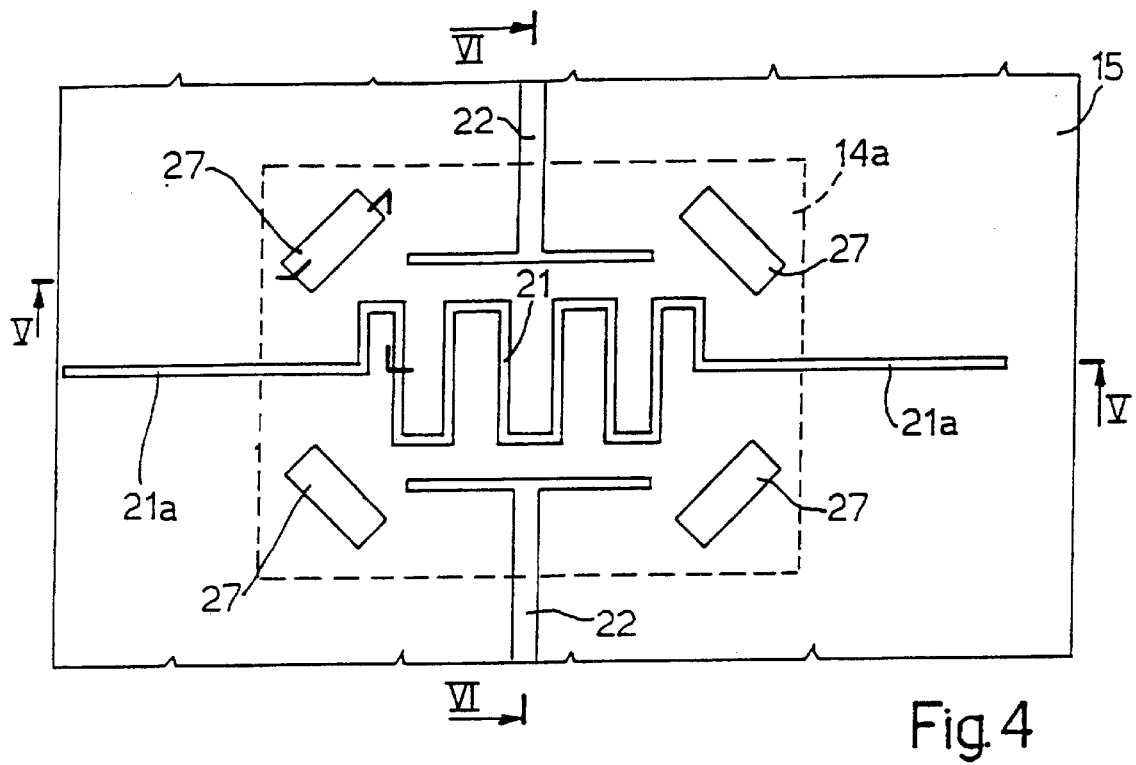
FIG. 4 shows a top view of the portion of FIGS. 2 and 3 in a successive step.
Figure 5:
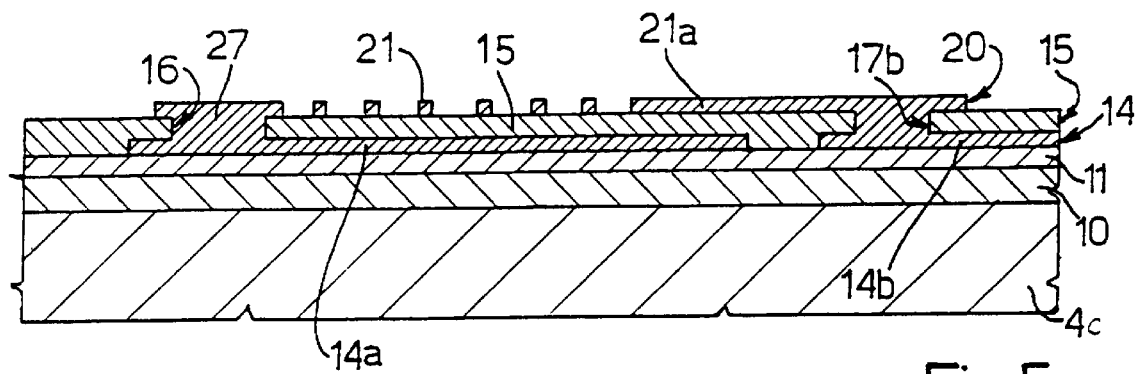
FIGS. 5 and 6 are views similar to those of views 2 and 3, corresponding to the section lines V—V and VI—VI of FIG. 4, respectively.
Figure 6:
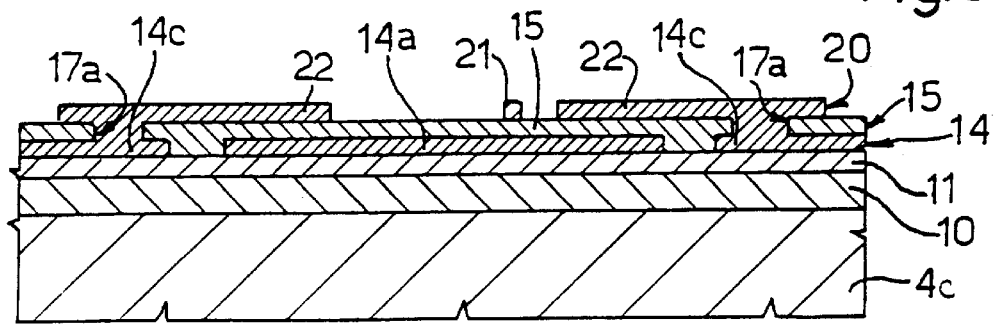
Figure 7:
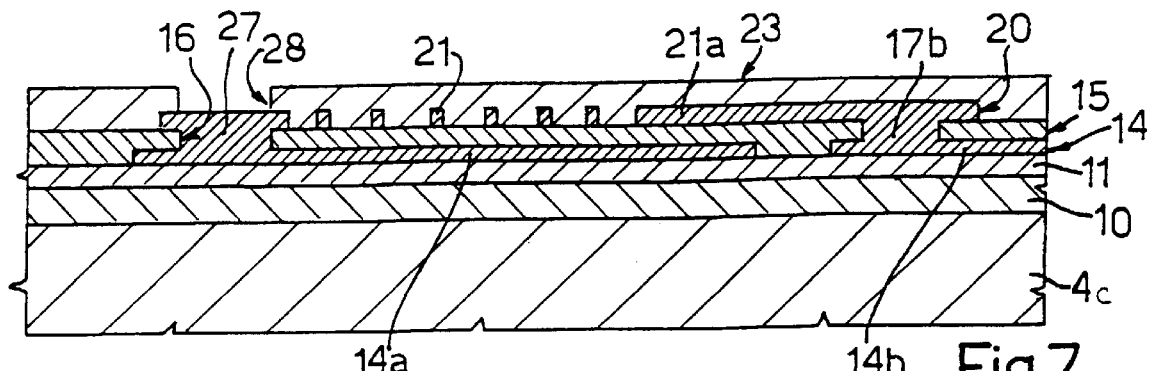
FIGS. 7 and 8 are views similar to those of views 5 and, respectively, 6, in a successive step.
Figure 12:
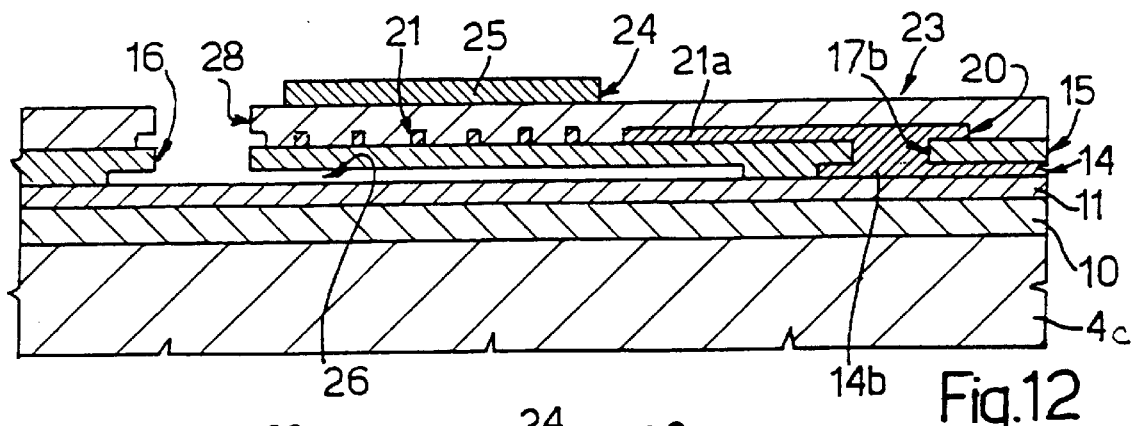
FIGS. 12 and 13 are views similar to those of FIGS. 7 and 8, in a final step of the manufacturing process.

On the intermetallic dielectric layer 15 is deposited a second metallic layer 20 which will fill the openings 16, 17a and 17b in the intermetallic dielectric layer 15. The second metallic layer 20 is preferably formed by a triple layer of titanium/platinum/chromium, which permits operating temperatures of the finished device which are greater than those which can be tolerated in the case of alurrinium metallizing. As shown in FIGS. 4–6, the second metallic layer 20 is then defined so as to form, above the sacrificial region 14a, a heater 21 of the coiled type, having contact electrodes 21a extending as far as the openings 17b, and filling them, so as to connect the heater 21 to the contact regions 14b. Second metallic layer 20 forms contact electrodes 22 for the sensor, extending from the sides of the heater 21 (but separated from it) as far as the openings 17a, and filling them, so as to form an electrical contact with the contact regions 14c. Second metallic layer 20 also fills regions 27 at the openings 16. The cross-section of FIGS. 5, 7 and 12 are not taken on a straight line, but goes through the regions 27 and the sensor 21 as shown by the bold marks of FIG. 4 for section line V—V.

Figure 8:
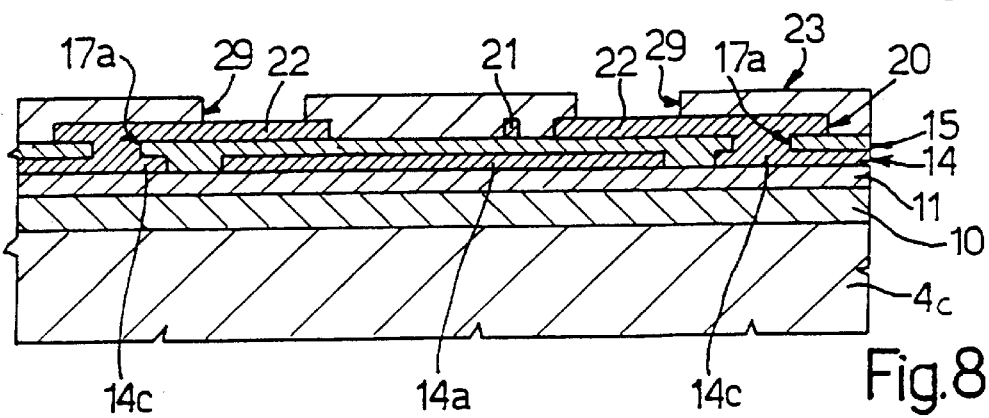

A dielectric passivation layer 23 (FIGS. 7 and 8) is then deposited which is subsequently removed above the regions 27 (openings 28), at the ends, close to the heater 21, of the contact electrodes 22 (openings 29) and at the contact pads (not shown) of the device.

In a first embodiment, the layer 23 is a material that is a thermal insulator as well as an electrical insulator, such as silicon dioxide.

In an alternate embodiment of the invention, the dielectric passivation layer 23 is a diamond or diamond-like structure, such as a carbon-like diamond. In some embodiments, the layer 23 may be two separate materials positioned on different parts of the chip. For example, one material under the sensor 24, the material being an electrical insulator and a thermal conductor, such as carbon-like diamond (CLD), and a second material over the circuits on the rest of the device, not under sensor 24, the second material being any of several passivation layers known in the art, such as silicon dioxide or silicon nitride.

Figure 9:
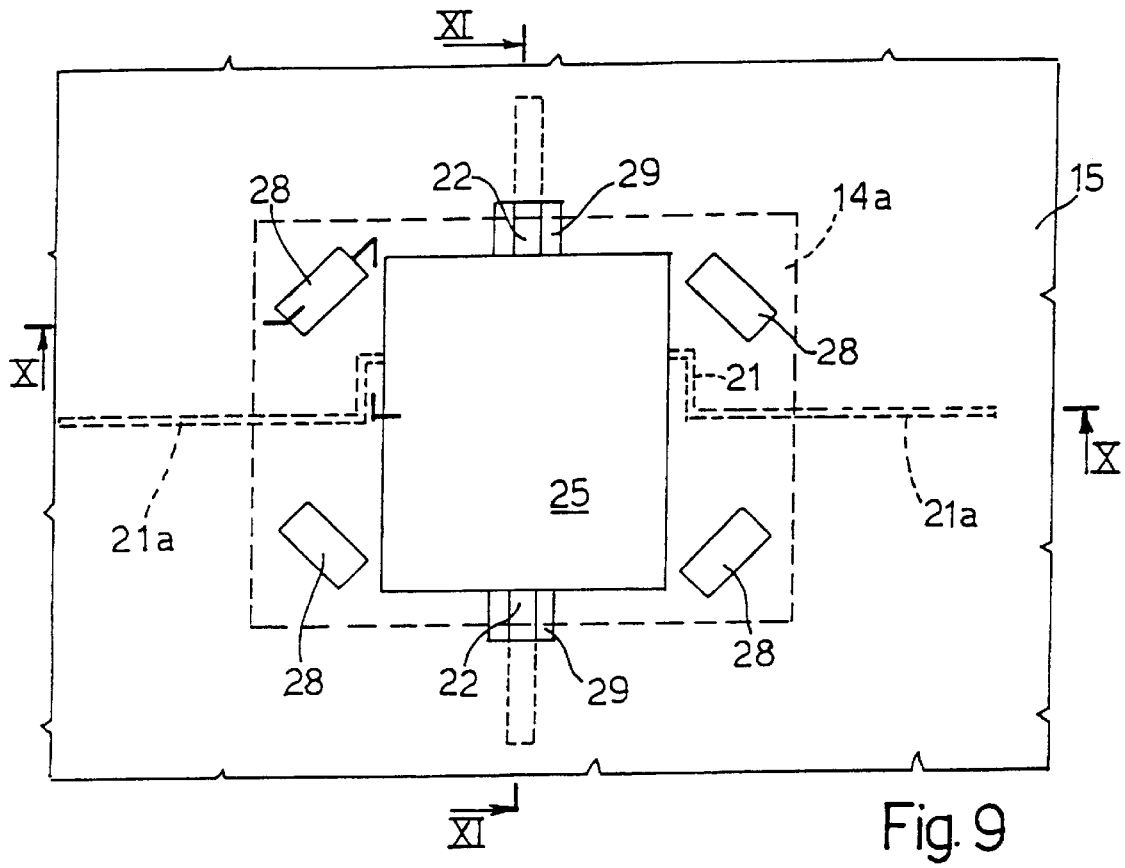
FIG. 9 shows a top view similar to FIG. 4 in a subsequent step.
Figure 10:
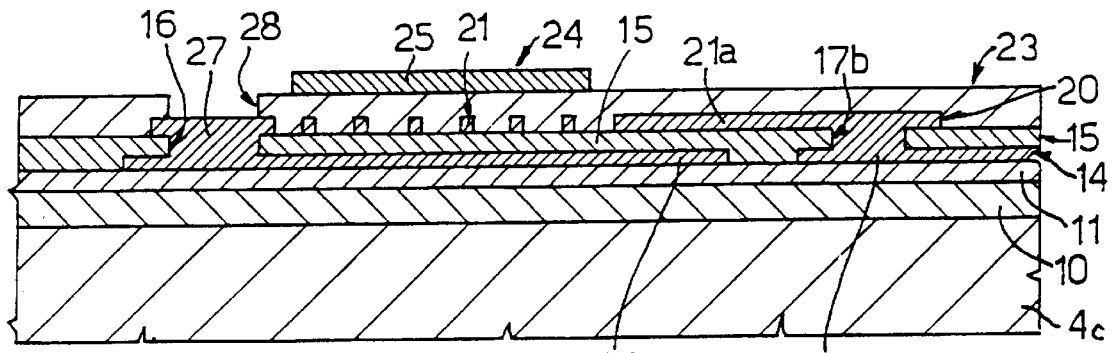
FIGS. 10 and 11 are views similar to those of FIGS. 7 and 8, corresponding to lines X—X and XI—XI of FIG. 9.
Figure 11:
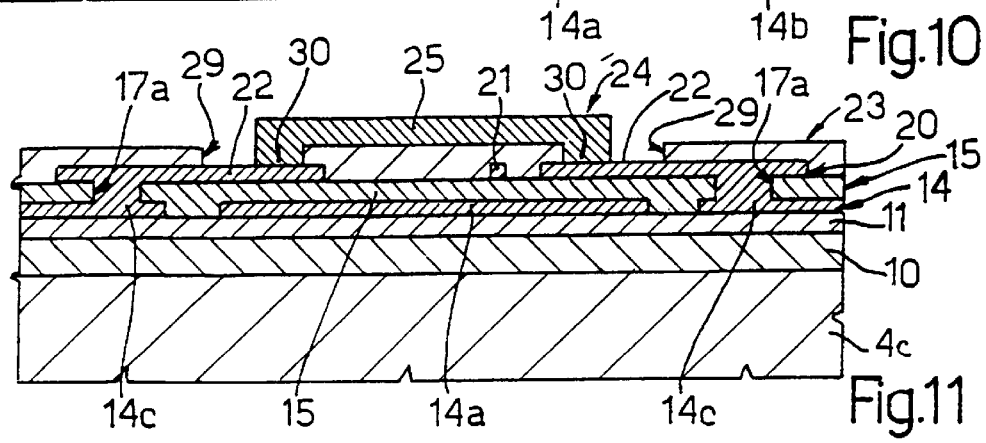

As shown in FIGS. 9, 10 and 11, a tin oxide film 24 is deposited (by "sputtering," for example) on top of the dielectric passivation layer 23. A catalyst layer (not shown), of platinum/palladium for example, having the purpose of reducing the activation energy of the film 24 and facilitating the chemical reaction between the molecules of gas and the tin oxide, may optionally be deposited on top of the film 24. Alternatively, a certain percentage of catalyst metal may be incorporated directly in the tin oxide film 24. The tin oxide film 24 and the optional catalyst layer are then defined by means of masking, so as to produce a sensitive element 25 extending over (but isolated from) the heater 21 and having contact regions 30 passing through the openings 29 and in direct contact with the uncovered portions of the contact electrodes 22, producing an electrical connection between the sensitive element 25 and the contact regions 14c.

Figure 13:
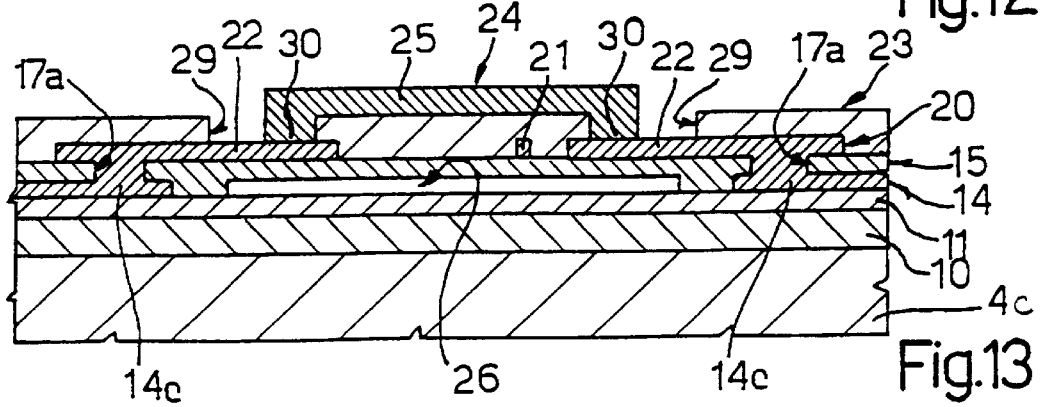

Subsequently, the structure is masked so as to cover the entire surface except for the zone at the regions 27. Wet etching is then carried out of the regions 27 and, through the etching openings 16, of second metallic layer 20 and the sacrificial region 14a. This causes removal of the entire region 14a under the heater element. After the removal of the masking layer, the suspended structure shown in FIGS. 12 and 13 is obtained, in which an air gap 26 with the function of thermal insulation is present in the place of the sacrificial region 14a.

In the final integrated device, the sensitive element 25 and the heater 21 are supported by the dielectric layer 15 and are disposed above the air gap 26, which insulates them thermally from the regions underneath.

The advantages which can be obtained with the manufacturing process and the sensor which have been described are as follows.

Firstly, the process described is completely compatible with planar microelectronics technology, enabling use to be made of its well-known advantages in terms of reliability, reproducibility and costs. Furthermore, the monolithic integration in a single chip of the sensor and of the associated control and signal processing circuits is possible.

The sensor described has superior spatial integration compared with the known solutions which use techniques of anisotropic etching from the front or the back of the substrate. As a result of this greater integration, the sensor is smaller and requires, for its operation, a smaller amount of energy than the known sensors.

The air gap which is present beneath the sensor, thanks to its low thermal conductivity, considerably increases the thermal resistance of the chemoresistive film with respect to the substrate, enabling the sensitive element 25 to reach the desired operating temperatures without excessive heating of other integrated structures on the device such as the circuits in epi layer 4a and the bipolar transistor 7 and other such structures in region 4b. The heater is on the same substrate but can now operate without detriment to the other parts of the device.

When the sensor is to be used in a continuous mode of operation, where the sensor is elevated to temperature and remains heated at a selected temperature for some time, the layer 23 can be any acceptable electrical insulator, such as silicon dioxide. Silicon dioxide has some thermal insulation properties. These can be taken into account so that the heater 21 is raised to the correct temperature to provide proper heating of the sensor 25. This may also be used when the sensible layer is added with post-processing techniques and operation in continuous mode is desired.

On the other hand, if the sensor is to be used in a pulsed operation mode, in which a sharp increase in temperature of the sensor 25 is required over a short time, then the preferred material for layer 23 has a high thermal conductivity, to permit rapid transfer of heat to (or from) sensor 25 via heater element 21. A layer 23 of a relatively good thermal conductor should thus be used under sensor 25, such as a diamond-like layer, carbon-like diamond or other good thermal conductor, as well as being electrical insulators.

Furthermore it will be clear that modifications and variants may be introduced to the process and the sensor described and illustrated here without thereby departing from the protective scope of the invention. In particular, the isolation regions in the epitaxial layer may be formed in a different manner; for example, they may be dielectric instead of junction in type; the electronic components integrated in the chip may be both of the bipolar type and of the MOS type; the type of conductivity of the various regions may vary with respect to that shown.

We claim:

1. An integrated semiconductor devices comprising:
   a substrate of semiconductor material;
   a chemoresistive gas microsensor disposed above said substrate and including a heater element and a gas sensitive element;
   an air gap positioned above said substrate and interposed between said microsensor and said substrate;
   first and second metallic contact regions disposed on the same level as and laterally with respect to said air gap, said first and second metallic contact regions being electrically and physically isolated with respect to said air gap, said first contact region being in electrical contact with said gas sensitive element and said second contact region being in electrical contact with said heater element; and
   a first insulating layer supporting said microsensor, interposed between said air gap and said microsensor.

2. The device according to claim 1 wherein said first insulating layer has first and second windows in a position laterally offset with respect to said heater; wherein it comprises:
   first electrode portions extending on said first insulating layer in continuation of said heater, said first electrode portions being electrically connected to said first metallic contact regions through said first windows;
   second electrode portions extending on said first insulating layer and electrically isolated with respect to said first portions with dielectric, said second electrode portions being electrically connected to said second metallic contact regions through said second windows;
   a second insulating layer, interposed between said heater element and said gas sensitive element, said second insulating layer having third windows; and
   said gas sensitive element comprising connection portions extending through said third windows and in direct electrical connection with said second metallic contact regions.

3. The device according to claim 2, further comprising openings extending laterally with respect to said heater element and to said gas sensitive element through said first and second insulating layer as far as said air gap.

4. The device according to one of claims 1–3 wherein said heater element extends according to a coiled line.

5. A semiconductor device comprising:
   a first insulating layer overlaying a substrate;
   a first material positioned over the first insulating layer;
   a heater overlaying the first material;
   a second insulating layer overlaying the heater; and
   a sensor overlaying the second insulating layer.

6. The device according to claim 5 wherein the first material is air.

7. The device according to claim 5 wherein the second insulating layer comprises a thermally conductive material.

8. The device according to claim 5 wherein the second insulating layer is a material that is a thermal insulator.

9. The device according to claim 5 wherein the first material comprises a thermally insulative material.

10. A semiconductor device comprising:
    a substrate of semiconductor material having a first insulating layer disposed thereon;
    a heater element position above the first insulating layer and spaced apart from the first insulating layer to form a gap therebetween;
    a second insulating layer overlaying the heater element; and
    a gas sensitive element overlaying the second insulating layer.

11. The device according to claim 10, further comprising first and second metallic contact regions electrically coupled to the gas sensitive element, the first and second metallic contact regions being electrically and physically isolated from the gap.

12. The device according to claim 11 wherein said comprising first and second metallic contact regions are disposed on the same level as and laterally with respect to said air gap.

13. The device according to claim 11, further comprising a transistor electrically coupled to the first metallic contact region.

14. The device according to claim 10, further comprising a material layer disposed between the heater element and the gap.

15. The device according to claim 14 wherein the material layer comprises a thermally insulative material.

16. The device according to claim 10 wherein the gap includes an opening extending to a surrounding environment.

17. The device according to claim 16 wherein the opening extends through the second insulating layer.

18. The device according to claim 10 wherein the second insulating layer comprises a thermally conductive material.

19. The device according to claim 10, further comprising openings extending laterally with respect to the heater element and to the gas sensitive element through the first and second insulating layers as far as the gap.

20. An integrated semiconductor device, comprising:
a substrate of semiconductor material having an insulating region disposed thereon;
a first insulating layer positioned above said insulating region and spaced apart from said insulating region to form an air gap therebetween;
a chemoresistive gas microsensor disposed above said first insulating layer and including a heater element and a gas sensitive element;
first and second metallic contact regions disposed on the same level as and laterally with respect to said air gap, said first and second metallic contact regions being electrically and physically isolated with respect to said air gap, said first contact region being in electrical contact with said gas sensitive element and said second contact region being in electrical contact with said heater element.

21. The device according to claim 20 wherein said insulating region includes a field oxide layer.

22. The device according to claim 20 wherein said insulating region includes a field oxide layer disposed on said substrate and a protective dielectric layer disposed on said field oxide layer.

23. The device according to claim 20 wherein said first insulating layer comprises a thermally insulative material.

24. The device according to claim 20 wherein said air gap includes an opening extending to a surrounding environment.

25. The device according to claim 20, further comprising openings extending laterally with respect to the heater element and to the gas sensitive element through the first insulating layer as far as the air gap.

* * * * *

UNITED STATES PATENT AND TRADEMARK OFFICE
CERTIFICATE OF CORRECTION

PATENT NO.    : 6,028,331
DATED         : February 22, 2000
INVENTOR(S)   : Ubaldo Mastromatteo and Benedetto Vigna It is certified that errors appear in the above identified patent and that said Letters Patent is hereby corrected as shown below:

On the cover page, item [75], after "Ubaldo Mastromatteo, Cornaredo;" please delete "Vigna Benedetto" and insert therefor "Benedetto Vigna"

Signed and Sealed this

First Day of May, 2001

Attest:

NICHOLAS P. GODICI

Attesting Officer       Acting Director of the United States Patent and Trademark Office